United States Patent
Denning et al.

(10) Patent No.: US 8,986,991 B2
(45) Date of Patent: Mar. 24, 2015

(54) HIGH YIELD SUSPENSION CELL LINE, SYSTEM AND METHOD FOR MAKING SAME

(71) Applicant: Expression Therapeutics, LLC, Tucker, GA (US)

(72) Inventors: Gabriela D. C. Denning, Atlanta, GA (US); Richard E Gautney, Atlanta, GA (US)

(73) Assignee: Expression Therapeutics, LLC, Tucker, GA (US)

( * ) Notice: Subject to any disclaimer, the term of this patent is extended or adjusted under 35 U.S.C. 154(b) by 0 days.

(21) Appl. No.: 13/932,391

(22) Filed: Jul. 1, 2013

(65) Prior Publication Data

US 2014/0011273 A1 Jan. 9, 2014

Related U.S. Application Data

(60) Provisional application No. 61/667,776, filed on Jul. 3, 2012.

(51) Int. Cl.
*C12N 5/07* (2010.01)
*C12N 5/10* (2006.01)
*C12N 5/071* (2010.01)
*C12N 15/85* (2006.01)

(52) U.S. Cl.
CPC ...... *C12N 15/85* (2013.01); *C12N 2740/15052* (2013.01)
USPC ............................ 435/352; 435/325; 435/369

(58) Field of Classification Search
None
See application file for complete search history.

(56) References Cited

U.S. PATENT DOCUMENTS

2004/0023333 A1* 2/2004 Hauser et al. ................ 435/69.6

* cited by examiner

*Primary Examiner* — Blaine Lankford
*Assistant Examiner* — Thomas J Visone

(57) ABSTRACT

A system and method of adapting host cells to suspension cell culture and suspension cell lines ATCC PTA-12593 and ATCC PTA-12461 produced thereby are disclosed. The method includes the serial replating of substantially undiluted culture cells onto a surface area until cell clumps are visualized and then, upon cell clumping, moving the cells into a suspension culture system.

3 Claims, 11 Drawing Sheets

| Platform | Roller Bottle | Bioreactor |
|---|---|---|
| Production format | 500 bottles | 2000 L |
| Daily harvest | 500 L | 500 L |
| Cell density | 170,000 per ml | 2 million per ml |
| FVIII expression rate | 100 units/$10^6$ cells/day | 100 units/$10^6$ cells/day |
| Specific activity | 10,000 units/mg | 10,000 units/mg |
| Daily productivity | 8.5 million units (0.85 g) | 100,000,000 units (10 g) |
| Run duration | 10 days | 30 – 300 days |
| Total yield | 85 million units (8.5 g) | 3 – 30 billion units (0.3 – 3 kg) |

FIG. 11

HIGH YIELD SUSPENSION CELL LINE, SYSTEM AND METHOD FOR MAKING SAME

RELATED APPLICATIONS

The present patent document claims the benefit of the filing date under 35 U.S.C. §119(e) of Provisional U.S. Patent Application Ser. No. 61/667,776, filed Jul. 3, 2012, which is hereby incorporated by reference in its entirety.

BACKGROUND

The manufacturing of recombinant protein-based biopharmaceuticals is a complex, labor and capital-intensive endeavor. Currently, mammalian cells are used for the production of most human proteins. Mammalian cells typically contain extensive post-translational modifications that may not be performed by unmodified prokaryotes and unmodified single-celled eukaryotes. Although mammalian cells such as Chinese hamster ovary cells and baby hamster kidney cells can faithfully biosynthesize most human proteins, the efficiency is dramatically lower than is achieved by bacterial or yeast cells.

Of the recombinant proteins currently marketed, fVIII is manufactured with the lowest efficiency and is by far the most expensive on a per unit mass basis (FIG. 1). Recombinant fVIII is the premiere treatment option for persons with the congenital X-linked bleeding disorder, hemophilia A. Treatment consists of 2-3 intravenous infusions per week of recombinant fVIII at a cost of approximately $100,000-$300,000 per year (Bohn R L, Avorn J, Glynn R J, Choodnovskiy I, Haschemeyer R, Aledort L M. Prophylactic use of factor VIII: an economic evaluation. Thromb Haemost. 1998; 79(5):932-7, incorporated herein in its entirety). Consequently, treatment access is limited to less than one-third of persons with hemophilia A worldwide. Historically, fVIII supply has been inadequate and price has remained exorbitant due to high research, development and manufacturing costs. One strategy for improving the care of hemophilia A, as well as other monogenic diseases that can be treated by protein replacement therapy, is to develop more efficient methods for recombinant protein manufacturing.

State-of-the-art recombinant h-fVIII products are produced typically by mammalian cells, e.g., BHK-21 or Chinese hamster ovary cells, in large-scale fermenting bioreactors. Several techniques may be used to maximize the production of recombinant h-fVIII including (1) amplification of the h-fVIII transgene using DHFR/methotrexate selection, (2) addition of fVIII stabilizing agents to the culture medium (e.g. bovine/human albumin or co-expression of vWf), and (3) maximizing cell growth/density by continuous-perfusion fermentation. FVIII may be purified from conditioned culture medium using a series of filtration, immunoaffinity, size-exclusion and ion-exchange chromatography steps. Often, viral inactivation procedures are incorporated into the purification protocol for added safety. Once purified, the bulk fVIII material may be formulated with stabilizing agents and may be freeze-dried prior to packaging. This standard manufacturing process is reviewed in Boedeker B G. Production processes of licensed recombinant factor VIII preparations. Semin Thromb Hemost. 2001; 27(4):385-94, incorporated herein by reference in its entirety.

First generation recombinant fVIII products were stabilized using human serum albumin that theoretically could harbor viral contaminants. To reduce the risk of viral contaminants, second and third generation fVIII products have emerged that are considered "animal-product free" and instead are stabilized with sucrose and other additives. Due to the perceived improved safety profile of newer generation recombinant products over both plasma-derived and first generation products, many previously-treated and the majority of previously-untreated patients have transitioned to second and third generation fVIII products. This demand has created multiple fVIII product shortages and lead to the implementation of strategies to temporarily ration fVIII supplies (Garber K. rFactor VIII deficit questioned. NatBiotechnol. 2000; 18(11):1133, incorporated herein by reference).

Several publications have stated that the standard level of recombinant human fVIII production is <1 unit/$10^6$ cells/day (Kaufman R J, Pipe S W, Tagliavacca L, Swaroop M, Moussalli M. Biosynthesis, assembly and secretion of coagulation factor VIII. Blood CoagulFibrinolysis. 1997; 8 Suppl 2:53-14.:S3-14, incorporated herein by reference). Typically, the final recombinant human fVIII product has a specific activity between 4,000-10,000 units per milligram protein and the cost of a single treatment for a 70 kg adult is $2,500-$5,000. Currently, fVIII products represent a 6-8 billion dollar annual market despite the fact that distribution is limited to less than one-third of the potential world market.

DESCRIPTION OF DRAWINGS

FIG. 11 compares recombinant FVIII production from BHK-M (adherent) and BHK-Ms (suspension) culture platforms.

DETAILED DESCRIPTION

Figure 1:
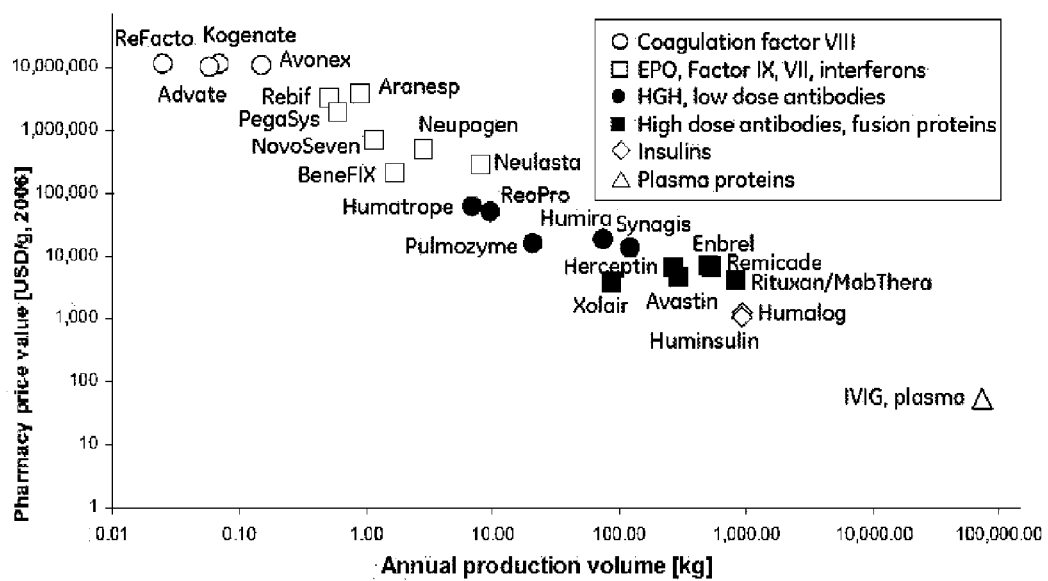
FIG. 1 is a graphical representation of the current landscape in biopharmaceutical manufacturing.

We disclose a novel method of adapting to suspension cell culture mammalian cell lines that were previously limited to adherent production culture systems, for example but not limited to, roller bottles. We also disclose novel cell lines designated ATCC PTA-12593 and ATCC PTA-12461 made by the methods disclosed herein that exhibit enhanced production (as compared to known systems and methods) in suspension culture of recombinant proteins. A suspension cell culture line. A suspension a cell culture line made by the method disclosed herein and designated BHK-MS throughout has been deposited with the ATCC and assigned accession number PTA-12953. A suspension cell culture line made by the method disclosed herein and designated BHK-MS-HA16 has been deposited with the ATCC and assigned accession number PTA-12461. The BHK cell line was derived from baby Syrian hamster (*Mesocricetus auratus*) kidney. In addition, we disclose a novel method and cell line for suspension cell virus production. The methods, systems, and cell lines disclosed are adaptable and adapted to serum-free and blood-protein free suspension culture environments.

The novelty and importance of our discovery cannot be underestimated. There are many biotherapeutics critical to human (and animal) health and welfare that are either unavailable or in shockingly limited supply due to profound and seemingly insurmountable manufacturing difficulties. The optimum cell line for producing these proteins, in some cases, may be limited to adherent cell production. Adherent cell production may be less efficient, less scalable, and otherwise less desirable for large-scale commercial biomanufacturing than other methods, for example, but not limited to, suspension cell culture. Therefore, the ability to adapt to suspension cell culture traditionally adherent cell lines, (for example but not limited to, adherent cell lines previously resistant to adaptation by known methods), is a significant achievement. Furthermore, the method and system disclosed is also a novel alternative method to the methods formerly and successfully used to adapt adherent cells to suspension cell culture.

Recombinant human fVIII is one example of a biotherapeutic that is notoriously difficult to manufacture.

Currently marketed recombinant human fVIII products are produced commercially at levels 100-1000 fold lower than other recombinant biotherapeutics such as, but not limited to, monoclonal antibodies. The low yield of fVIII expression has a strong influence on product pricing and availability. In fact, recombinant fVIII has the highest price point and lowest annual production volume of any major biopharmaceutical at a pharmacy price of $10,000,000 per gram and an annual worldwide total production volume of less than 0.5 kilograms.

One consequence of low fVIII expression efficiency is that less than one-third of persons with hemophilia A world-wide have access to fVIII. For those excluded from treatment, hemophilia A represents a lethal disease with median mortality in the teenage years.

To address the manufacturing difficulties posed by biotherapeutics such as fVIII, elements of the manufacturing system may be optimized—for example but not limited to—the construct, the expression vector, the cell line, the cell culture conditions, and etc. To illustrate, we have characterized and patented a novel recombinant fVIII construct that is biosynthesized more efficiently than human fVIII on a per cell basis. (See U.S. Pat. No. 7,635,763 (incorporated herein by reference in its entirety, See also, Spencer H T, Denning G, Gautney R E, Dropulic B, Roy A J, Baranyi L, et al. Lentiviral Vector Platform for Production of Bioengineered Recombinant Coagulation Factor VIII. Mol Ther. 2010, which is incorporated herein in its entirety)). In our proof of concept experiments disclosed herein, we refer to the recombinant fVIII molecule used as ET-801. ET-801 is a polypeptide comprising an amino acid sequence at least about 93% identical to SEQ ID NO: 19 of U.S. Pat. No. 7,635,763.

Turning to the cell line, we have found that the BHK-M cell line may out produce other commonly used mammalian cell lines, e.g., Chinese hamster ovary cell line DG44, or BHK-21 cell lines, for the production of recombinant fVIII, including but not limited to ET-801. However, the BHK-M is derived from a parental cell line (ATCC PTA-4506) that is permissive only to growth under adherent conditions. As we disclose herein, adapting BHK-M cells to suspension cell culture may increase its production efficiency, scalability, and usefulness in large-scale biomanufacturing processes.

We disclose herein a method of adapting an adherent cell line to a suspension cell-based biomanufacturing platform for biotherapeutics, which may be simple or complex biotherapeutics. We also disclose a method and system optimized to produce high yields (compared to currently known systems) of simple and/or complex biotherapeutics; enhanced production (compared to currently known systems) of recombinant proteins in suspension cell culture; and production of virus in suspension cell culture. Additionally, we disclose a cell-line for high yield production of products and viruses.

The novel system and method disclosed herein has displayed extraordinary performance over known systems, as demonstrated by the disclosed data. For example, we demonstrate that this system, method, and cell line out-produces currently known manufacturing methods by a surprising and extraordinary degree which may be at least 5% and up to 1000% greater than known methods. For example, the system, method, and cell line may result in an increase in protein production that comprises at least about 5%-1000%, 5%-900%, 5%-800%, 5%-700%, 5%-600%, 5%-500%, 5%-400%, 5%-300%, 5%-200%, 5%-100%, 5%-75%, 5%-50%, 5%-25%, 10%-1000%, 10%-900%, 10%-800%, 10%-700%, 10%-600%, 10%-500%, 10%-400%, 10%-300%, 10%-200%, 10%-100%, 10%-75%, 10%-50%, 10%-25%, 20%-1000%, 20%-900%, 20%-800%, 20%-700%, 20%-600%, 20%-500%, 20%-400%, 20%-300%, 20%-200%, 20%-100%, 20%-75%, 20%-50%, 20%-25%, 30%-1000%, 30%-900%, 30%-800%, 30%-700%, 30%-600%, 30%-500%, 30%-400%, 30%-300%, 30%-200%, 30%-100%, 30%-75%, 30%-50%, 30%-1000%, 30%-900%, 30%-800%, 30%-700%, 30%-600%, 30%-500%, 30%-400%, 30%-300%, 30%-200%, 30%-100%, 30%-75%, 30%-50%, 40%-1000%, 40%-900%, 40%-800%, 40%-700%, 40%-600%, 40%-500%, 40%-400%, 40%-300%, 40%-200%, 40%-100%, 40%-75%, 40%-50%, 50%-1000%, 50%-900%, 50%-800%, 50%-700%, 50%-600%, 50%-500%, 50%-400%, 50%-300%, 50%-200%, 50%-100%, 50%-75%, 50%-60%; 60%-1000%, 60%-900%, 60%-800%, 60%-700%, 60%-600%, 60%-500%, 60%-400%, 60%-300%, 60%-200%, 60%-100%, 60%-75%, 70%-1000%, 70%-900%, 70%-800%, 70%-700%, 70%-600%, 70%-500%, 70%-400%, 70%-300%, 70%-200%, 70%-100%, 70%-75%, 80%-1000%, 80%-900%, 80%-800%, 80%-700%, 80%-600%, 80%-500%, 80%-400%, 80%-300%, 80%-200%, 80%-100%, 100%-1000%, 100%-900%, 100%-800%, 100%-700%, 100%-600%, 100%-500%, 100%-400%, 100%-300%, 100%-200%, 100%, 200%-1000%, 200%-900%, 200%-800%, 200%-700%, 200%-600%, 200%-500%, 200%-400%, 200%-300%, 200%-200%, 200%, 300%-1000%, 300%-900%, 300%-800%, 300%-700%, 300%-600%, 300%-500%, 300%-400%, 300%, 400%-1000%, 400%-900%, 400%-800%, 400%-700%, 400%-600%, 400%-500%, 400%, 500%-1000%, 500%-900%, 500%-800%, 500%-700%, 500%-600%, 500%, 600%-1000%, 600%-900%, 600%-800%, 600%-700%, 600%, 700%-1000%, 700%-900%, 700%-800%, 700%, 800%-1000%, 800%-900%, 800%, 900%-1000%, 900% greater expression of protein compared to the expression of the same protein in a the adherent cell line from which the suspension cell line is derived, and/or compared to expression of the same protein in a known protein expression system.

While our examples demonstrate that our novel system and method does and may further increase manufacturing capacity and scalability of fVIII, it is clear (from our demonstration with GFP) that our novel method, system, and cell line may also be applied to increase yield, manufacturing capacity, and scalability of other proteins. We anticipate that this platform will and can be utilized by us and others to manufacture alternative recombinant biopharmaceuticals, for example, but not limited to, coagulation factors IX and VIIa.

Furthermore, while we demonstrate herein the successful application of the method with, baby hamster kidney-derived (BHK-M) cell line, (a resulting cell line designated herein BHK-Ms, a line from which is deposited with the ATCC having the ATCC number 12953 and a second resulting cell line which is deposited with the ATCC having the ATCC number PTA-12461) and HEK-293T cell line, our novel method, system, may also be applied to increase yield, manufacturing capacity, and scalability of other cell lines (whether or not they were previously amenable to suspension culture). The disclosed method has improved efficiency and adapts adherent cells to suspension in exponentially less time than currently implemented methods, reducing the cost and increasing the availability of biotherapeutics. The disclosed method and system results in a suspension cell line that may be maintained up to two months and/or indefinitely in a suspension culture system, for example, but not limited to a culture system utilizing serum and blood-component free production medium.

In one variation, a method and system for adapting host cells to suspension culture may be performed by a method comprising:
  a. Growing one or more adherent host cells (e.g., in a growth supporting media) on a first culture dish (e.g., a culture dish with a surface);
  b. Growing the cells to a level of confluency, for example but not limited to 20%-100%, 30%-100%, 40%-100%, 50%-100%, 60%-100%, 70%-100%, 80%-100%, and/or 100% confluency;
  c. Dissociating the cells from the culture dish;
  d. Resuspending the cells in a growth supporting medium;
  e. Replating on a culture dish and growing the cells in a growth supporting medium;
  (this step may be removed, cells may be resuspended in the original culture dish),
  f. Repeating steps (a)-(e) until the cells have formed clumps; and
  g. transferring the cells to a suspension culture for example but not limited to spinner or shaker flask;
  h. agitating the cells for example but not limited to shaking or stirring.

Figure 2:
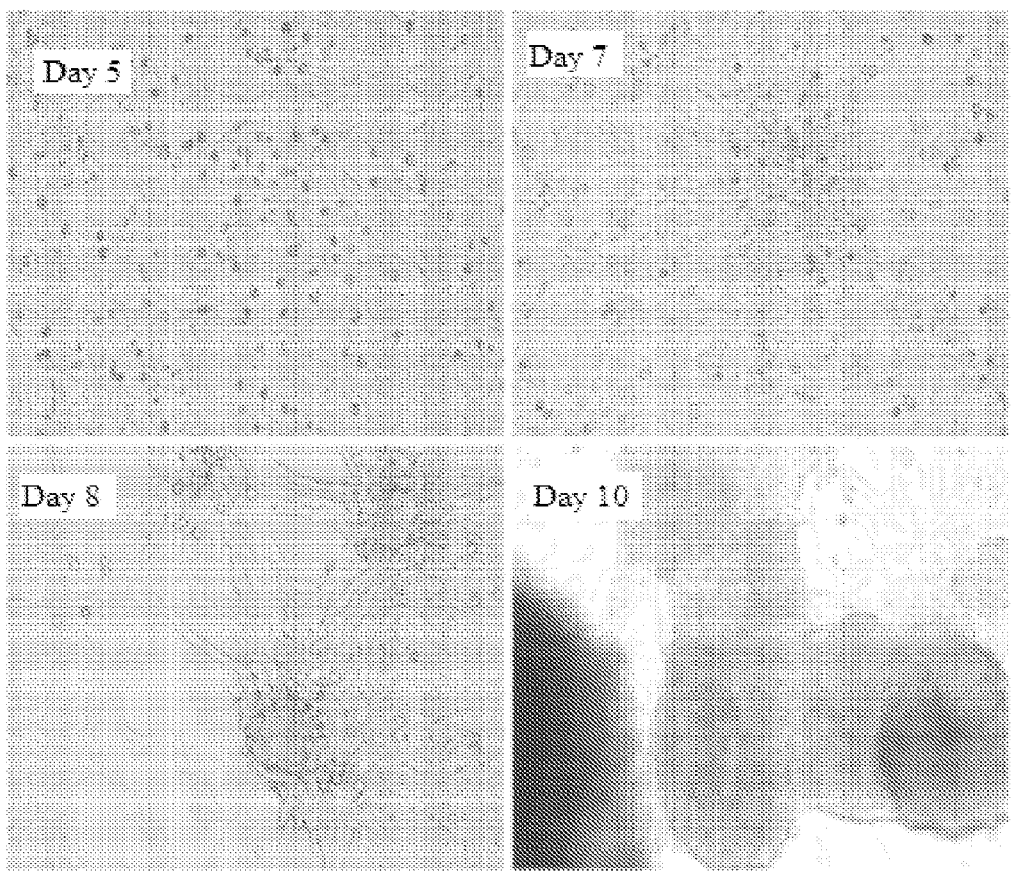
FIG. 2 depicts the conversion of BHK-M cells to BHK-Ms cells. BHK-M cells are adapted to suspension using a method described herein.
Figure 4:
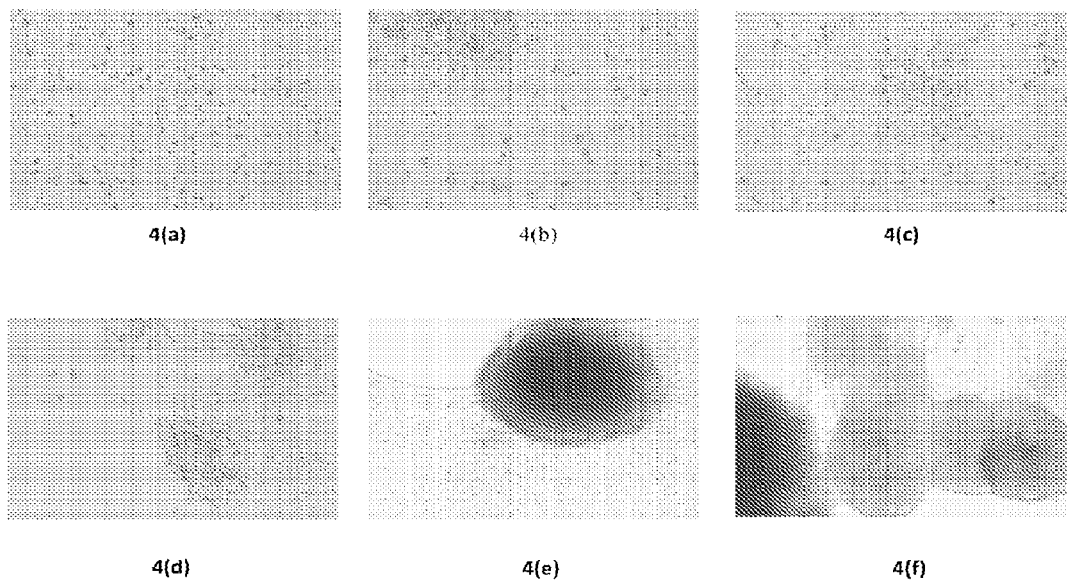
FIG. 4 depicts conversion to suspension of adherent HEK-293T cells.

In another variation, a method and system for adapting host cells to suspension cell culture may be performed according to the following steps:
  a. one or more host cells are grown on a first culture dish having a growth supporting surface,
  b. permitting the host cells to grow on the culture dish until they have reached a level of confluency, for example, the host cells may be grown on the culture dish until they have reached about 60%-about 100% confluency,
  c. removing the growth supporting medium from the cells once the host cells have reached a level of confluency,
  d. optionally washing the cells, for example with a buffer (e.g., an isotonic buffer solution, for example, Phosphate-Buffered Saline, or some other buffer),
  e. dissociating the cells from the culture dish, for example but not limited to, adding an effective amount of cell dissociation solution to the cells (e.g., trypsin or EDTA), mechanically dissociating (e.g., cell scraper, pipet, and etc.) or any other mechanical, chemical, enzymatic or other manner;
  f. incubating the cells under growth supporting conditions, for example but not limited to about 37° C. and 5% $CO_2$ until cells dissociate from culture dish;
  g. resuspending the cells in an effective amount of the growth supporting medium;
  h. optionally, plating the resuspended cells into a new culture dish, for example but not limited to, a culture dish with the same surface area as the first culture dish, alternatively or additionally, a culture dish with a larger or smaller surface area than the first culture dish;
  i. growing the cells for about 1 to about 24 hours, or about 1 to about 48 hours under growth supporting conditions, for example but not limited to about 37° C. and 5% $CO_2$;
  j. repeating steps (c) through (i) at least about 1 time or until the cells have formed visible clumping (e.g., for a visual example of the clumping, see FIG. 2 (slide marked "Day 10") and FIG. 4, for example, FIGS. 4(e) and 4(f).)
  k. transferring the cells to a suspension culture for example but not limited to spinner or shaker flask;
  l. agitating the cells for example but not limited to shaking or stirring.

In another variation, a method and system for adapting host cells to suspension cell culture may be performed according to the following steps:
  a. one or more host cells are grown on a first culture dish having a growth supporting surface,
  b. permitting the host cells to grow on the culture dish until they have reached a level of confluency, for example, the host cells may be grown on the culture dish until they have reached about 60%-about 100% confluency,
  c. removing the growth supporting medium from the cells once the host cells have reached a level of confluency,
  d. optionally washing the cells, for example with a buffer (e.g., an isotonic buffer solution, for example, Phosphate-Buffered Saline, or some other buffer),
  e. dissociating the cells from the culture dish, for example but not limited to, adding an effective amount of cell dissociation solution to the cells (e.g., trypsin or EDTA), mechanically dissociating (e.g., cell scraper, pipet, and etc.) or any other mechanical, chemical, enzymatic or other manner;
  f. incubating the cells under growth supporting conditions, for example but not limited to about 37° C. and 5% $CO_2$ until cells dissociate from culture dish;
  g. resuspending the cells in an effective amount of the growth supporting medium (without removing them from the original culture dish);
  h. growing the cells for about 1 to about 24 hours, or about 1 to about 48 hours under growth supporting conditions, for example but not limited to about 37° C. and 5% $CO_2$;
  i. repeating steps (c) through (h) at least about 1 time or until the cells have formed visible clumping (e.g., for a visual example of the clumping, see FIG. 2 (slide marked "Day 10") and FIG. 4, for example, FIGS. 4(e) and 4(f).)
  j. transferring the cells to a suspension culture for example but not limited to spinner or shaker flask;
  k. agitating the cells for example but not limited to shaking or stirring.

During further research we came to the surprising result that the method may be further simplified. In one example, the cells are grown to a level of confluency, the growth supporting medium is removed, and new medium is directly added without intervening disassociation steps. In a second example, the cells are grown to a level of confluency, the growth supporting medium is removed, a dissociation enzyme is added and removed without removing the cells from the plate, and new growth supporting medium is added.

The host cell may be any type of mammalian cell, for example but not limited to COS, CHO, HeLa, BHK-M, BHK-21, HEK-293T, murine myelomas, as well as transformed primary cell lines, hybridomas, normal diploid cells, and cell strains derived from in vitro culture of primary tissue, among many others known in the art. Any mammalian cell that has previously been shown to be amenable to adaption to suspension cell culture may be used in the disclosed method. More importantly, the method has shown to successfully adapt cell lines that have not previously been adapted to suspension culture and are thus limited to adherent growth, such as but not limited to BHK-M.

The mammalian cells may be genetically modified mammalian cells expressing a recombinant polypeptide and/or recombinant virus of interest, or modified mammalian cells expressing a recombinant polypeptide and/or recombinant virus of interest. For example, genetic modification of the mammalian cell lines, for example, BHK-Ms, may be performed using, among other methods, electroporation, cationic liposomes, cationic polymers, and lentiviral vector-mediated transduction. Genetic modification may be performed on the host cell before adaption to suspension or after adaption to suspension. Modifying the cells before adaption to suspension may have some advantages of being able to more reliably choose optimum clones.

The growth supporting medium may refer to a nutrient solution which permits the growth and maintenance of eukaryotic cells and that may provide one or more of the following categories: (1) salts (e.g., sodium, potassium, magnesium, calcium, etc.) contributing to the osmolality of the medium; (2) an energy source, which may be in the form of a carbohydrate such as but not limited to glucose; (3) amino acids, which may be some or all essential amino acids; (4) vitamins and/or other organic compounds; and (5) trace elements, for example, inorganic compounds that may be required at very low concentrations (e.g., micromolar range). The growth supporting solution may optionally be supplemented with one or more of the components from any of the following categories: (1) animal serum; (2) hormones and other growth factors such as, for example, insulin, transferrin, and epidermal growth factor; and (3) hydrolysates of plant, yeast, and/or tissues, including protein hydrolysates thereof.

Additionally or alternatively, the growth supporting medium may be serum-free medium, chemically-defined medium, or medium lacking animal derived components. Chemically defined medium are media in which all components have a known chemical structure. Chemically-defined medium are available from commercial suppliers such as, for example, Sigma and Gibco. Any growth supporting medium that supports cell growth and maintenance under the conditions provided herein may be used. One skilled in the art will be able to suitably select for a particular culture the appropriate medium as well as the other culture variables (see, e.g., Mather J. P. et. Al. (1999) "Culture media, animal cells, large scale production," Encyclopedia of Bioprocess Technology: Fermentation, Biocatalysis, and Bioseparateion, Vol. 2:777-785 which is hereby incorporated by reference in its entirety).

The disclosed method may be used to adapt cells to serum-free media directly without applying serum-reduction techniques. For example, the growth supporting media used in all of the method steps may be serum-free growth supporting media. Alternatively, the serum containing media may be completely replaced by serum-free media at any step, for example but not limited to, during the serial re-plating and/or resuspension steps and/or when the cells are removed to suspension culture flasks. In another example, the serum containing medium may be completely replaced by serum-free medium by removing the serum containing medium and replacing it with serum free medium without removing the cells from the culture dish.

Cell dissociation may be achieved by many known methods, for example but not limited to adding an effective amount of cell dissociation solution to the cells (e.g., trypsin or EDTA), mechanically dissociating (e.g., cell scraper, pipette, and etc.) or any other mechanical, chemical, enzymatic or other manner. Cell dissociation may occur without removing the cells from the original culture dish. For example, this step may involve applying a cell dissociation solution to the surface of the cells (e.g., trypsin or EDTA), immediately pouring off the cell dissociation solution, incubating the treated cells for an appropriate amount of time (e.g., 5 minutes) under appropriate conditions, and resuspending the cells by merely adding new growth supporting media. All of these steps may take place in the original culture dish and without ever removing the cells from the original culture dish.

A cell dissociation enzyme may comprise a chaotropic agent, or an enzyme, or both. The washing step may optionally be deleted or may be performed on some rounds of the protocol and not on others. The advisability of the washing step is easily determined on a case-by-case basis with the consideration that the washing step may break up the forming cell clumps and may therefore be discontinued or perhaps omitted.

The amount of time that the cells are grown out between each dissociation step may vary depending on the nature of the starting adherent cell line. The important factor is that the cells are dissociated and resuspended until the cells form visible clumps (e.g., for a visual example of clumping, see FIG. 2 (slide marked "Day 10") and FIG. 4, for example, FIGS. 4(e) and 4(f)).

The following examples illustrate and provide data supporting the use of the system and method to achieve adaption of adherent cell lines to suspension and also the enhanced growth and production characteristics in an exemplary system, derived BHK-Ms and HEK-293T cells at 100-1000 ml spinner flask scale. The examples are meant to be illustrative and do not limit the scope of the invention.

Example 1

In a first example, we provide an exemplary variation of the method. We also provide data illustrating the use of the method to adapt to suspension an adherent cell line and achieve enhanced growth and production in the exemplary system. In this nonlimiting example, the exemplary host cell is derived BHK-M cells (derived from a parental cell line (ATCC PTA-4506)) expressing ET-801 which upon adaptation to suspension are designated BHK-Ms, at 100-1000 ml spinner flask scale. In this example BHK-Ms cells expressing ET-801 are grown in suspension according to the disclosed method. Resulting fVIII production is measured and compared to adherent cell-based fVIII production.

Host cells were generated using a novel lentiviral expression system for the production of ET-801 (Spencer H T, Denning G, Gautney R E, Dropulic B, Roy A J, Baranyi L, et al. Lentiviral Vector Platform for Production of Bioengineered Recombinant Coagulation Factor VIII. Mol. Ther. 2010, incorporated herein by reference in its entirety, referred to hereinafter as "Spencer 2010"). For this exemplary experiment, we obtained a BHK-M clone, designated 3-10, that expresses recombinant fVIII (ET-801) at a mean level of 160 units/$10^6$ cells/24 hr. In this preliminary experiment we illustrate the extraordinary protein production results using the novel system and method to adapt to suspension clone 3-10 (made according to the procedure described in Spencer 2011 which is incorporated herein in its entirety) by performing a small scale manufacturing run.

Anchorage dependent BHK-M cells were grown at 37° C. and 5% $CO_2$ on 100 mm×20 mm cell culture treated dishes (Corning #430167) in 10 mL of Advanced Dulbecco's Modified Eagle's Medium/F12 (DMEM/F-12, Invitrogen #12634) supplemented with 10% Fetal Bovine Serum (FBS, Invitrogen #10082), 1% GlutaMAX-I (Invitrogen #35050), and 1% Penicillin-Streptomycin (Invitrogen #15140) by volume (hereafter referred to as DMEM Complete or DMEM:F12 Complete). When the Cells had grown to 100% confluency the DMEM Complete media was removed, the cells were washed once with 3 mL of (1×) Dulbecco's Phosphate-Buffered Saline (dPBS, Invitrogen #14190), 500 μL of TrypLE Express (Invitrogen #12605) was added evenly across the dish, and the dish was incubated at 37° C. and 5% $CO_2$ for 5 minutes. After the incubation period the cells were gently resuspended in 5 mL of DMEM Complete and all the cells (without substantial dilution or splitting) were transferred to a new dish of the same surface area as the first dish, with an additional 25 mL of DMEM Complete and allowed to continue growing in the incubator overnight at 37° C. and 5% $CO_2$. This plating process was repeated every day for 4 days, until the cells started to form three dimensional structures due to the increasing cell density creating a lack of surface area on the dish for the cells to settle into monolayers. (See FIG. 2) In some variations, suspension culture was achieved even when the re-plating and washing steps were deleted from the protocol.

At this point the cells were transferred to suspension culture. A 125 mL spinner flask (Corning #3152) was prepared by filling with 120 mL of DMEM Complete supplemented with an additional 1.25 mL Pluronic F-68 (10% solution, Invitrogen 24040). Cells were washed with dPBS, detached from the culture dish with TrypLE, incubated, and carefully resuspended as before, then transferred to the before mentioned spinner flask and maintained at an agitation of 60 rpm within a 37° C. and 5% $CO_2$ incubator. Cell viability was monitored daily by staining for dead cells with Trypan Blue (STEMCELL Technologies #07050). Every third day the media within the flask was exchanged by removing 80 mL of the remaining media and replacing with 85 mL of fresh DMEM Complete supplemented with 850 μL of Pluronic F-68.

In this preliminary experiment, we demonstrated that BHK-M cells can be adapted to suspension using the disclosed method involving serial re-plating and/or serial re-suspending of adherent BHK-M cells. Over 10 days of serial re-plating and/or serial re-suspending in the original plate, while culturing at 37° C., 95% humidity, and 5% $CO_2$, the cells adopt a highly clumped state and their growth becomes independent of surface attachment space within the tissue culture vessel. When the cells become independent of surface attachment, the cells are switched to shaker or spinner flasks and are maintained under identical culture conditions with the addition of moderate rotation (60-75 rpm). Within 1-2 days of suspension culture, the cells begin to expand with a doubling time of 24-48 hr. At this point, the cells are adapted to suspension culture, given the designation "BHK-Ms" cells, and can be maintained in serum containing or serum-free medium for greater than two months (likely indefinitely) as determined empirically. The cells were observed entering suspension and achieving high-density without the use of growth inhibition substances.

FIG. 2 depicts visually the conversion of BHK-M cells to BHK-Ms cells by the experimental method disclosed above. BHK-M cells are adapted to suspension using the disclosed method involving serial re-plating and/or re-suspending of adherent BHK-M cells. Over 10 days of serial re-plating and/or re-suspending, the cells adopt a highly clumped state (as seen in FIG. 2) and their growth becomes independent of surface attachment space within the tissue culture vessel. At this point, the cells can be seeded into shaker or spinner flasks set for moderate rotation (60-75 rpm). Within 1-2 days of suspension culture, the cells begin to expand with a doubling time of 24-48 hr.

In this experimental variation, the resulting BHK-Ms clone 3-10 demonstrated robust and sustained expansion for more than 40 days at 1 liter scale. During the serum-free production phase, approximately 1,000,000 units of fVIII were harvested from the system. This represents an approximately 50-fold improvement over commercial recombinant human fVIII production systems without any significant optimization.

Figure 3:
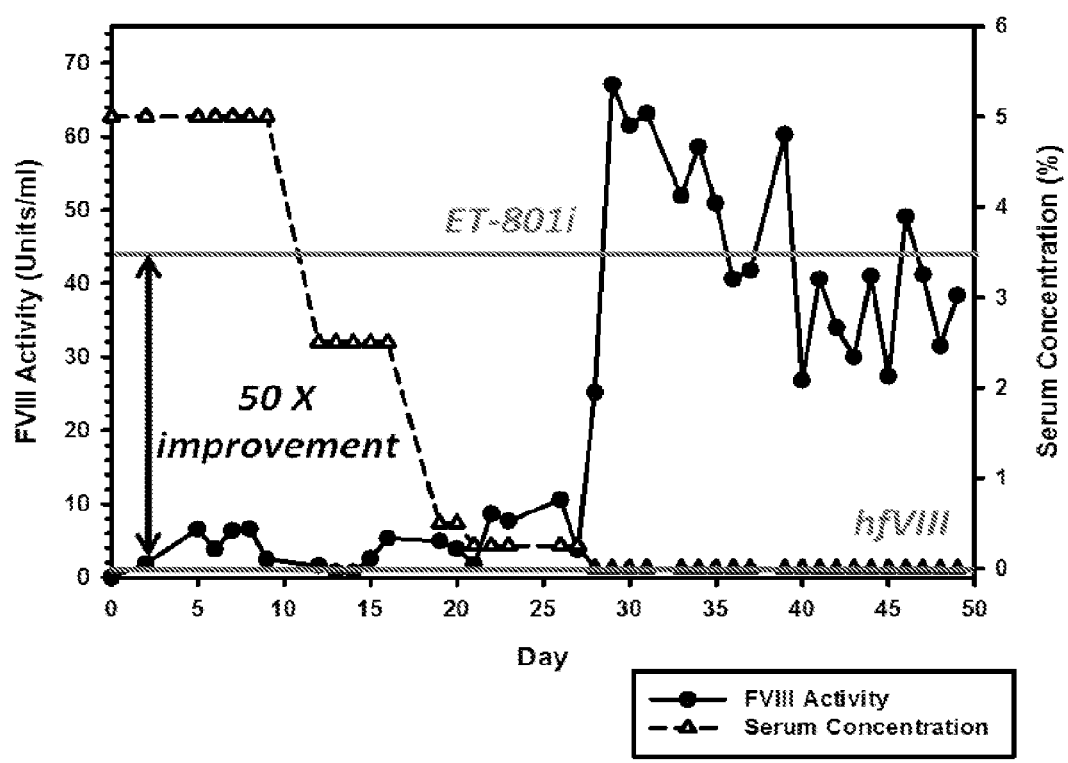
FIG. 3 depicts the expression of recombinant fVIII from BHK-Ms cells in serum-free media.

FIG. 3 demonstrates the 50-fold improvement resulting expression of recombinant fVIII from BHK-Ms cells generated by the disclosed method. While in suspension, complete media exchanges were performed daily and the fVIII activity concentration of each collection was determined by one-stage coagulation assay. The horizontal lines represent the mean serum-free fVIII production level for ET-801 (indicated by "ET-801" above line) according to the disclosed method. The horizontal line indicated by hfVIII represents the mean of published production levels for recombinant human (h) factor VIII.

This cell line provides enhanced product yield, ability to grow in suspension culture, and enhanced ability to produce virus over its parental cell line.

Example 2

In a second example, we provide an exemplary variation of the method and data illustrating the use of the system and method to adapt to suspension and achieve enhanced grown characteristics in an exemplary system, HEK-293T adherent cells. In this example HEK-293T cells are adapted to suspension according to a variation of the disclosed method under designated conditions. The cell line resulting from the following method is designated HEK-SC-293T. The HEK-SC-293T cell line provides enhanced product yield, ability to grow in suspension culture, and enhanced ability to produce virus over its parental cell line.

The method according to this example follows:
a. Starting with a frozen naïve HEK-293T attached cell line,
b. Thawing in 10 mL DMEM/F-12 complete (with 5% Glutamax, 10% FBS) in a corning 10 cm dish @37° C., 5% $CO_2$;
c. Growing cells to confluence in a 10 cm dish in effective amount of growth supporting medium, such as DMEM/F-12 complete (1-2 days);
d. Clumping the cells by repeating the following steps every day until clumps form which are substantially not attached to surface of plate:
 i. Remove all media,
 ii. Wash cells with PBS (this step is optional and was discontinued after the first couple of cycles),
 iii. Add 700 μL TrypLE (Trypsin analogue, Invitrogen #12605) iv. Incubate for 5 min @37° C., 5% $CO_2$,
 v. Carefully transfer all cells to a new 10 cm dish with increasing amounts of DMEM/F-12 complete depending on cell density, trying not to break up dumps (the transfer step may be deleted, the cells may be resuspended in the original culture dish, e.g., without removing the cells to a new 10 cm dish), vi. Incubate overnight @ 37° C., 5% $CO_2$, vii. Repeat steps (i) to (vi) until cells have formed clumps, viii. After cells have formed clumps, transfer cells to a 125 mL spinner flask (Corning #3152) with 50 mL media (DMEM/F-12 complete in this case) supplemented with 1% V/V Pluronic F-68, ix. Incubate overnight @ 37° C., 5% $CO_2$ with moderate rotation (60 rpm).

e. Under this example, after adapting the cells to suspension, daily media exchange of the suspension culture consisted of pelleting cells @ 400 G for 5-10 minutes, removing spent media, resuspending all cells in 100 mL media supplemented with 1% V/V Pluronic F-68. Incubating for overnight @ 37° C., 5% $CO_2$ with moderate rotation (60 rpm).

f. Measuring cell density by comparing protein levels of an aliquot of clumped cells lysed with RLA (Promega #Z3051) to a standard curve of protein levels at known cell densities of non-clumped cells using bicinchoninic acid assay (BCA assay) kit (See Thermo Scientific #23225, kit protocol, which is incorporated herein in its entirety).

FIGS. 4(a)-4(f) demonstrate through photographic documentation the success of the novel disclosed method in this experimental variation. FIG. 4(a) shows the starting material, confluent adherent HEK-293T cells. FIG. 4(b) shows day 1-2 of serial replating, at which time increased cell density and cell piling was observed. FIG. 4(c) shows day 2-3 of continued serial replating, at which time more cell piling was observed. FIG. 4(d) shows day 3-4 of serial replating, during which time cell aggregates started to grow above adherent cell monolayer. FIG. 4(e) shows day 4-5 of serial replating, during which time cell aggregates began to grow larger. FIG. 4(f) shows days 5-8 of re-plating at which time cell aggregates became anchorage independent.

The culture may be maintained indefinitely by repeating step (e), e.g., the pelleting step, daily while only resuspending a fraction (usually ~80%) of the cells.

The cells according to this Example 2 were transfected after they were adapted to suspension.

While the above method may be used to produce a suspension cell line from many adherent cell lines, the resulting cell line from this particular example with the specific parameters stated above, the method of making and using being fully described above, is designated HEK-SC-293T. This cell line provides enhanced product yield, ability to grow in suspension culture, and enhanced ability to produce virus over its parental cell line.

Example 3

In a third example, we provide an exemplary variation of the method and data illustrating ability of the cell line resulting from the disclosed method to produce recombinant virus. Transduction for titering may be performed by known methods or as described in Spencer 2011, incorporated herein by reference in its entirety.

In a further variation, we disclose a method and cell line, (designated HEK-SC-293T the method of making and using fully disclosed herein and available, among other means, by contacting the inventors and/or assignee) for high yield virus production, for example, by transducing with the virus of interest a cell line according to the method disclosed herein.

The following example illustrates the production and concentration of third-generation lentivirus from cells adapted to suspension according to the disclosed methods. Reference to, for example, container sizes and all amounts, of course, may be modified and adjusted to scale up or scale down the production. The method may be demonstrated by the following steps:

a. Seeding cells for transfection:

i. Starting a new flask containing HEK-SC-293T suspension cells at 1×10⁶ cells/mL (for example, as determined by BCA assay) in 50 mL Complete DMEM:F12 ii. Incubating cells at 37° C., 5% $CO_2$, 60 rpm b. Transfecting (Day 1):

i. In a 15 ml conical tube combine total amount of plasmid DNA (see Table 1 below) in a final volume of 5 ml of, for example, OPTI-MEM I (Gibco) or similar product. Filter sterilize through a filter, for example, a 0.22 μm filter, into a new 15 ml conical tube

TABLE 1

| Plasmid | Amount of Plasmid DNA/Triple Flask (mg) | # of Spinner Flasks | Total Amount of Plasmid DNA(mg) |
| --- | --- | --- | --- |
| Transfer Plasmid | 80 | 1 | 80 |
| pKgagpol (pLTG1294) | 52 | 1 | 52 |
| pKg (pLTG1292) | 28 | 1 | 28 |
| pKrev (pLTG1293) | 20 | 1 | 20 |
| Total | 180 | N/A | 180 | ii. In a separate 15 ml conical tune combine 144 μl of 10 mg/ml polyethlyleneimine (PEI) (see Table 2 below for PEI calculation) with 5 ml of, for example, OPTI-MEM I (Gibco) or similar product. Filter sterilize through a filter, for example, a 0.22 μm filter, into a new 15 ml conical tube.

TABLE 2

Figure 5:
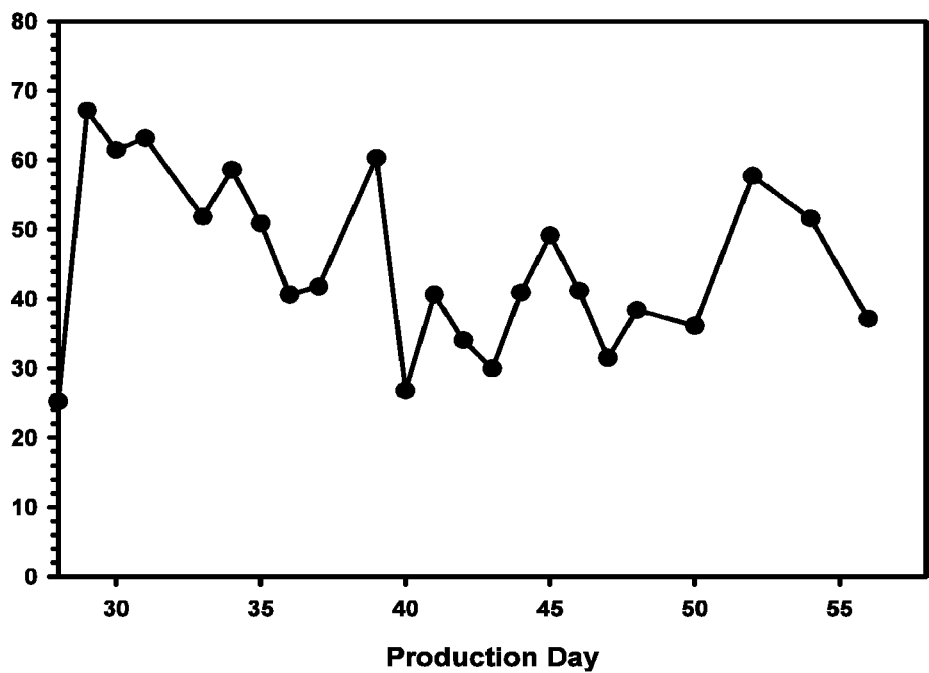
FIG. 5 is a chart showing evidence of high level fVIII expression from suspension adapted cells.

| PEI Stock Concentration | Amount of PEI/mg Plasmid DNA | Total Amount of Plasmid DNA (mg) | Total Amount of PEI (ml) |
| --- | --- | --- | --- |
| 10 mg/ml | 0.8 ml | 180 | 144 | iii. Combine plasmid DNA and PEI mixtures and incubate at room temperature for 20 minutes.

iv. Pellet suspension cells, for example HEK-293T suspension cells, in 50 ml conical tube at 1500 rpm for 10 minutes, discard conditioned medium.

v. While pelleting, add DNA/PEI mixture to 50 ml of fresh DMEM:F12 complete (lacking 1% Penicillin/Stretomycin) for a final volume of ~60 ml and thoroughly combine to ensure a homogenous mixture.

vi. Resuspend suspension cells, for example, HEK-293T suspension cells, in spinner flask using media from flask.

vii. Transfect the cells overnight by incubating in a 37° C. incubator with 5% $CO_2$ at 60 rpm.

c. Post Transfection (Day 2):
  i. Pellet transfected suspension cells as outlined previously and carefully decant transfection medium from cells and replace with 50 ml of DMEM:F12 complete.
  ii. Continue to culture cells at 37° C. incubator with 5% $CO_2$.
d. Virus Collection/Harvest (Day 3 and 4):
  i. Examine condition of cells for evidence of transfection, for example, with GFP cells check cells under a fluorescent microscope. For fVIII, one may, for example, check media for clot times.
  ii. If evidence shows that the cells are expressing the desired product, proceed as follows:
    1. Pellet cells at 1,500 rpm for 10 minutes (e.g., to remove cell debris)
    2. Decant virus containing medium into a sterile centrifuge bottle and reseed suspension cells, for example, HEK-293T suspension cells, back into the spinner flask with 50 ml of fresh DMEM:F12 complete and continue to culture cells in a 37° C. incubator with 5% $CO_2$ at 60 rpm.
    3. Filter the virus containing medium through a filter, for example, but not limited to, a 0.45 mm filter and store at 4° C. (up to about 4 days) until ready for virus concentration.
    4. Collect for 2 days by repeating steps outlined above.
  iii. Optionally concentrate, resuspend, and store virus.
  iv. The following Table illustrates the ability of cell lines adapted to suspension according to the disclosed method to produce functional virus, as measured by qPCR transgene copy number analysis of transduced BHK-M cells as described in Spencer 2011. Collected virus was subdivided by sequential day of virus collection and average titer for the non-concentrated virus containing media was calculated for each day. Estimated concentrated titer was then calculated by multiplying the non-concentrated titer by the concentration rate:

was measured and plotted on FIG. 5. Each data point represents the fVIII concentration from the complete 1 liter media harvest. No change in cell viability was observed suggesting that cell survival under these conditions is indefinite. In total, over 1 million units of fVIII activity were collected during this production run. Due to the high concentration of ET-801 in the starting material, it was possible, for the first time, to obtain highly purified material using a single cation-exchange chromatography procedure. Approximately 4.9 mg of highly purified ET-801 was isolated with 830-fold purification. The final material was calculated to have a specific activity of 3,000 units/nmol or 17,700 units/mg using a molar extinction coefficient at 280 nm of 254,955 $M^{-1}$ $cm^{-1}$ based on the predicted tyrosine, tryptophan, and cysteine content.

The purity of ET-801 was assessed by SDS-PAGE and compared to recombinant BDD human fVIII. A small amount of single chain material, which was sensitive to cleavage by thrombin, was present. No major contaminants were observed. Purified ET-801 was assessed for glycosylation, interaction with vWf, and activity decay following activation by thrombin. Treatment of ET-801 with thrombin and endoglycosidase PNGase F resulted in a change in $M_r$ for the A1 and A3-C1-C2 (light chain) protein fragments. No change in $M_r$ of the A2 domain was observed following PNGase F treatment. These data suggest a glycosylation pattern for ET-801 that is consistent with what has been described previously for recombinant BDD human and BDD porcine fVIII (Doering et al. Journal of Biological Chemistry. 2004. 279(8): 6546-6552, incorporated herein by reference in its entirety).

To confirm the in vivo functionality of the ET-801 produced, hemophilia A mice were infused with either saline or ET-801 at a dose of 290 units/kg, which was empirically determined to restore circulating fVIII activity to near normal murine levels. Following administration of saline or ET-801, the mice were subjected to a hemostatic challenge using tail transection and total blood loss was determined over a 40 minute period. Hemophilia A mice injected with saline alone had a mean blood loss of 29.6 mg/g body weight. In contrast,

TABLE 3

| Virus Collection Day | Virus Sample (μl) | Mean QTY | Copies | ml Virus | Titer (TU/mL) | "Concentrated" Titer | Average titer | Average Concentrated Titer |
|---|---|---|---|---|---|---|---|---|
| | mock | 0.2 | 2.4E−05 | 0 | N/A | N/A | N/A | N/A |
| Day #1 | 50 | 1.89 | 2.3E−04 | 0.05 | 3361.310452 | 8.40E+05 | | |
| | 100 | 10.02 | 1.2E−03 | 0.1 | 8910.140406 | 2.23E+06 | 6.45E+03 | 1.61E+06 |
| | 200 | 15.95 | 1.9E−03 | 0.2 | 7091.653666 | 1.77E+06 | | |
| Day#2 | 50 | 1.19 | 1.4E−04 | 0.05 | 2116.380655 | 5.29E+05 | | |
| | 100 | 3.57 | 4.3E−04 | 0.1 | 3174.570983 | 7.94E+05 | 3.14E+03 | 7.85E+05 |
| | 200 | 9.29 | 1.1E−03 | 0.2 | 4130.49922 | 1.03E+06 | | |
| Day#3 | 50 | 0.656 | 7.9E−05 | 0.05 | 1166.677067 | 2.92E+05 | | |
| | 100 | 1.21 | 1.5E−04 | 0.1 | 1075.975039 | 2.69E+05 | 1.35E+03 | 3.37E+05 |

Example 4

The following example and associated data further demonstrates high-level fVIII expression from cells adapted to suspension according to the disclosed methods. The following example is for illustrative purposes only and is not intended to limit the disclosure to particular scale or quantities, etc.

An ET-801 expressing BHK-M clone, designated 3-10, was adapted to serum-free suspension culture according to the method disclosed herein—thus becoming what we designate a BHK-Ms cell. The BHK-M clone was expanded and grown at 1 liter scale for 30 days and the fVIII concentration mice infused with ET-801 displayed a blood loss of 0.1 mg/g body weight, which was significantly less than controls (P=0.029).

While the above method may be used to produce a suspension cell line from many adherent cell lines, the resulting cell line from this particular example with the specific parameters stated above, the method of making and using being fully described above, is designated BHK-MS-310-ET801, and is available by contacting the inventors and/or assignee. This cell line provides enhanced product yield, ability to grow in suspension culture, and enhanced ability to produce virus over its parental cell line.

Example 5

Figure 6:
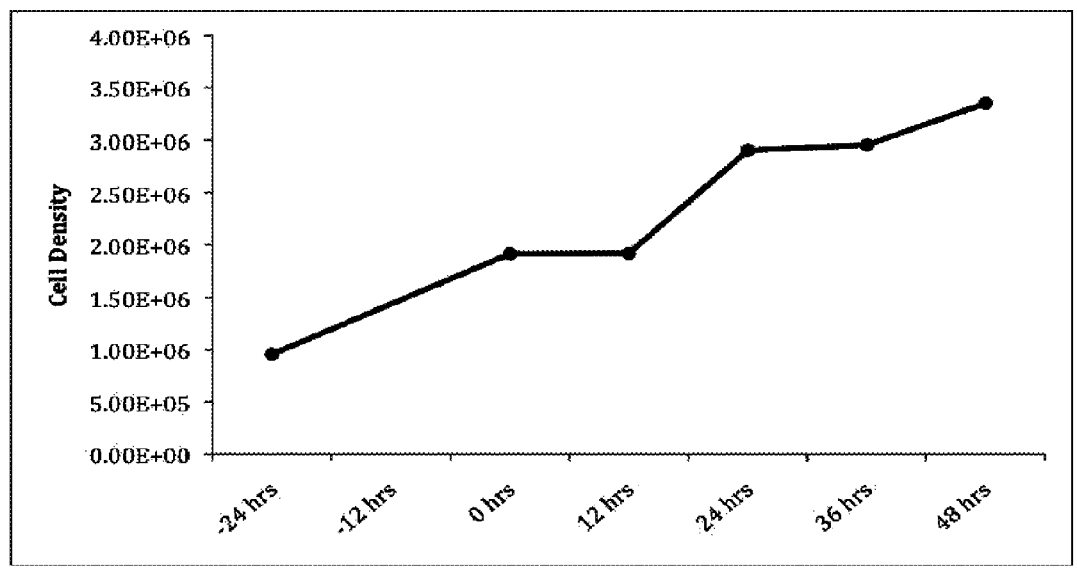
FIG. 6 is a plot depicting the results of optimized feeding schedule.

The following example and associated data illustrate the effect on cell density of an optimized feeding schedule. In this example, suspension cells were re-fed with fresh media every 12 hours instead of every 24-48 hours as illustrated in above examples. Using a 12 hour feeding schedule, we demonstrate that a higher cell density may be achieved and maintained as illustrated by FIG. 6.

Example 6

The following data characterizes an additional BHK-M clone adapted to suspension, designated P14, which was genetically modified by polymer facilitated transfection of a mammalian expression plasmid, serial transduction using a lentiviral vector, encoding a recombinant fVIII transgene, the product of which is referred to herein as ET-3 (ET-3 is a polypeptide comprising an amino acid sequence at least about 99% identical to SEQ ID NO: 19 of U.S. Pat. No. 7,635,763).

The resulting cell line from this particular example with the specific parameters stated above, the method of making and using being fully described in the examples above in combination with the methods of Spencer 2011, is designated BHK-MS-P14, and is available by contacting the inventors and/or assignee. This cell line provides enhanced product yield, ability to grow in suspension culture, and enhanced ability to produce virus over its parental cell line.

Figure 7:
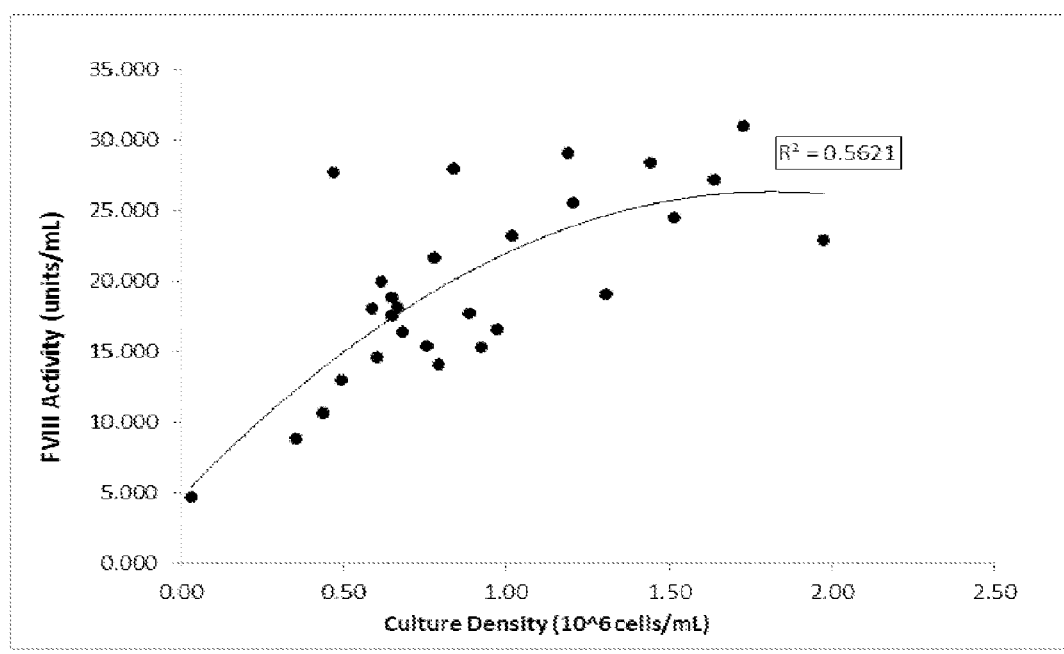
FIG. 7 is a plot characterizing an additional clone adapted to suspension using methods disclosed herein.

FIG. 7 illustrates fVIII activity (ET-3) as a function of culture density.

Figure 8:
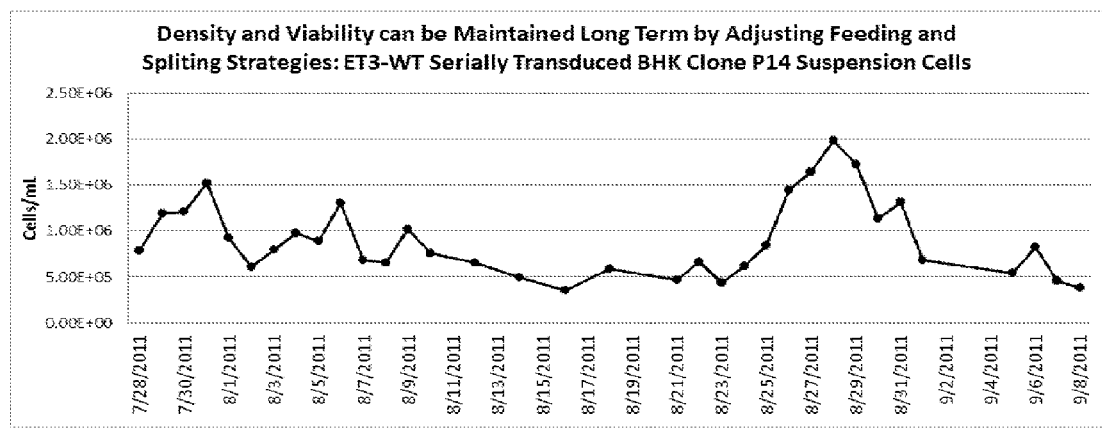
FIG. 8 is a graph of density and viability in an additional clone adapted to suspension using methods disclosed herein.

FIG. 8 illustrates the long-term growth and stability of the BHK-MS-P14 suspension culture. Density determinations were made by measuring total protein levels using the bicinchoninic acid (BCA) protein assay and comparing them to known BHK protein/cell standards.

Figure 9:
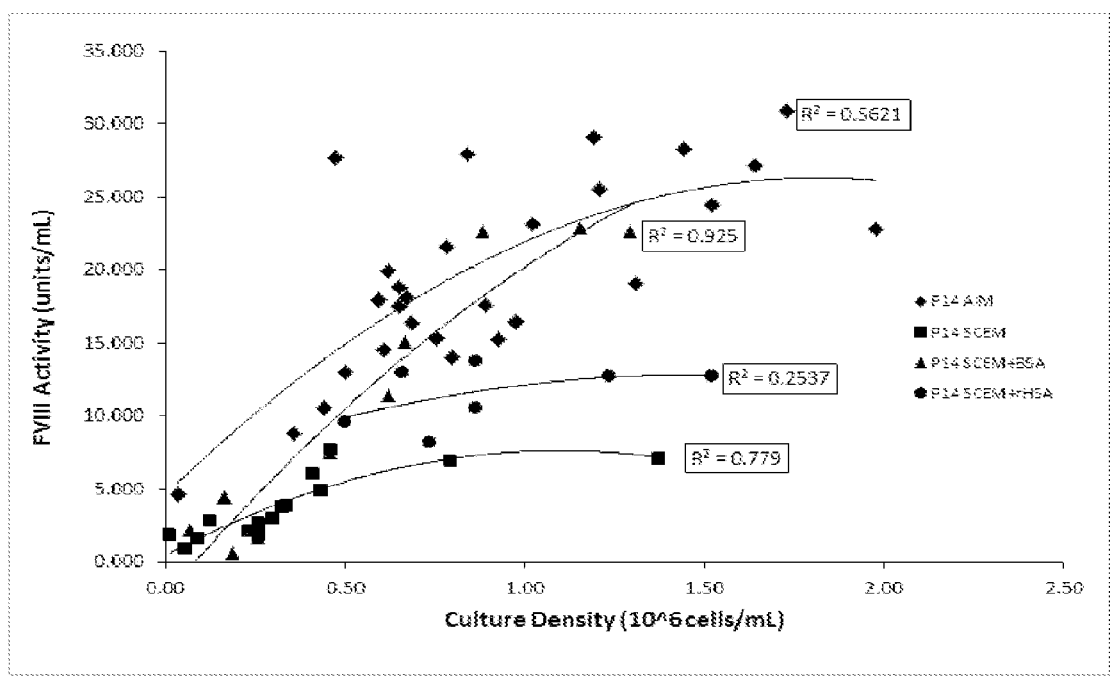
FIG. 9 is a graph of fVIII activity versus density in a clone adapted to suspension using methods disclosed herein.

FIG. 9 illustrates that the P14 clone is capable of efficient fVIII production in a variety of media, including but not limiting to, in serum-free or chemically-defined media supplemented with blood derived or recombinant albumin.

Example 7

In this example, we demonstrate that the cells adapted to suspension according to this method may be genetically modified to express a foreign transgene other than a recombinant fVIII molecule. For example, GFP.

Figure 10:
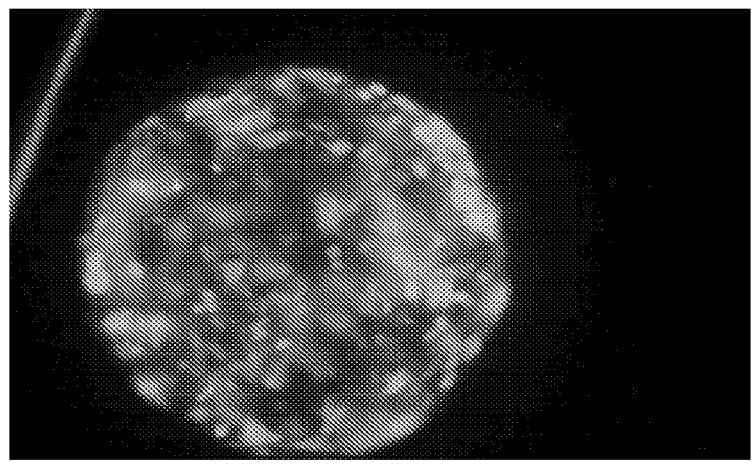
FIG. 10 is an image of a GFP transfected, GFP virus producing cell adapted to suspension using methods disclosed herein.

To demonstrate the value of the BHK-Ms cells according to the disclosed methods, we show that they readily can be genetically modified, e.g., to express a diversity of recombinant proteins. Therefore, we illustrate the efficiency of BHK-Ms genetic modifications using the cationic polymer PEI under standard transfection conditions. FIG. 10 demonstrates significant genetic modification of suspension HEK-SC-293T cell using PEI and a plasmid encoding green fluorescent protein (GFP) as a reporter. FIG. 10 is a GFP transfected, GFP producing HEK-293T adapted to suspension—according to the disclosed methods.

Example 8

The following is a proposed variation of the disclosed method for pilot production. For example, for pilot production, an adherent cell line adapted to suspension by the disclosed method, for example a BHK-Ms clone expressing ET-801, may be scaled up to, for example but not limited to, a 50 liter bioreactor (e.g., Xcellex) containing 10 liters of BHK-Ms production medium. Five to 10 liters of conditioned media may be harvested daily, clarified by filtration and frozen at −80° C. ET-801 may be purified from the conditioned media using a novel single-step ion-exchange chromatography protocol that we have developed and described previously (Spencer H T, Denning G, Gautney R E, Dropulic B, Roy A J, Baranyi L, et al. Lentiviral Vector Platform for Production of Bioengineered Recombinant Coagulation Factor VIII. Mol. Ther. 2011, incorporated herein in its entirety). As stated above, the purification of commercial full length recombinant human fVIII may involve an immuno-affinity step that may complicate the validation process due to the presence of another biological product in the purification, e.g., an anti-human fVIII monoclonal immunoglobulin. The use of the purification process we describe in Spencer 2011 may also lead to a reduction in manufacturing costs and therefore reduced cost of goods. The fVIII preparation may be analyzed for purity, processing, specific activity and the kinetics of decay following thrombin activation as described previously (Spencer H T, Denning G, Gautney R E, Dropulic B, Roy A J, Baranyi L, et al. Lentiviral Vector Platform for Production of Bioengineered Recombinant Coagulation Factor VIII. Mol. Ther. 2011) and below.

Example 9

The following exemplary cell line demonstrates that the cells adapted to suspension using the disclosed method are also compatible with plasmid systems. In this example, cells were transfected with a plasmid. Cells were transfected with a fVIII expressing plasmid. Factor VIII expressing clones were selected for adaptation to suspension culture. The clone selected was designated HA-16. The resulting suspension cell line is thus designated BHK-MS-HA16, a cell line of which is deposited with the ATCC and has the ATCC Patent Deposit Designation PTA-12461.

In this example, method of adapting cells to suspension culture was followed as disclosed herein. However, PBS was not used to wash the cells during the clumping process.

Further Considerations Regarding Novelty

According to the Examples and disclosure we demonstrate a method of adapting adherent cells to suspension culture. We also disclose novel cell lines produced by the disclosed method and demonstrate the superior production capabilities of suspension cell lines produced according to the disclosed methods. To further illustrate the surprising and extraordinary production results, the results disclosed herein may be compared against the results obtained in the current market by major market fVIII manufacturers. For scale and productivity comparison, Baxter, Inc announced in January 2006 that the cumulative sales of their third generation recombinant h-fVIII product, ADVATE™, surpassed 1 billion units (approximately 100 grams) since its approval by the FDA and European Commission in 2003-2004. As FIG. 1 depicts, the estimated annual production of each commercial recombinant fVIII products is 100-200 grams.

In comparison, our exemplary pilot-scale fVIII production run may be performed by seeding BHK-Ms clone 3-10 into a 1 liter spinner flask, which may be grown to a density of, for example, but not limited to, approximately $10^6$ cells/ml. The entire culture may then be used to seed a 50 liter bioreactor (e.g., Xcellerx) containing 10 liters of BHK-Ms production medium. Based on an expected cell density of $2 \times 10^6$ cells/ml in production phase, we estimate the daily ET-801 production using the following calculation:

$$\text{Daily } fVIII \text{ production} = \frac{2{,}000{,}000 \text{ cells}}{\text{ml}} * \frac{100 \text{ units}}{1{,}000{,}000 \text{ cells}} * 10{,}000 \text{ ml} = 2{,}000{,}000 \text{ units}$$

Therefore, we expected and demonstrated that over the course of a 30 day production run, 300 liters of conditioned medium containing approximately 60,000,000 units of fVIII activity will be collected. With a previously determined specific activity of 17,700 units/milligram (Spencer 2011), we expected and demonstrated a product yield in excess of 3 grams.

As demonstrated, in one 30 day 1 L run we collected over 1,000,000 units of fVIII. It is clear that, scaled up to biomanufacturing scale (e.g., Bayer runs 10 or more 200 L bioreactors in parallel at any given time), cells produced according to our disclosure could produce 1 billion units in one 30 day 1000 L run. In other words, what it took Bayer nearly 3 years to accomplish with its extensive manufacturing capabilities and staff, our method could accomplish in a 30 day 1000 L run.

Therefore the method, system, and cell lines disclosed herein promise to significantly reduce the cost and increase the availability of critically needed biotherapeutics such as but not limited to, fVIII. As a further example, Bayer has stated that at its Berkeley site, it takes more than 1000 people approximately 250 days to manufacture one lot of its fVIII product, KOGENATE FS. This represents 200 grams of product. Our disclosed method is capable of producing far more product in less time using fewer resources. For example, the estimated annual production of fVIII is 100-200 grams. We have demonstrated that we can produce, at laboratory scale with very limited resources and in 30 days, over one tenth of the estimated annual production of fVIII.

FIG. 11 depicts two manufacturing schemes, one based on roller bottle production of ET-801 and the other based on a single tank bioreactor. This emphasizes the benefits of suspension cell growth in recombinant protein manufacturing. Based on conservative estimates, BHK-Ms-based manufacturing may increase product yield more than 2-fold, 10-fold, 20-fold, 30-fold, 40-fold, 50-fold, 60-fold, or even 100-fold over BHK-M based roller bottle manufacturing. This key development may overcome the technical and economic entry barriers to the recombinant protein pharmaceutical marketplace, which may increase the supply of factor VIII to the ⅔ of those with hemophilia A whom currently have no access.

Disclosure of Exemplary Experimental Protocol for Characterizing fVIII Product.

Purification and Biochemical Analysis of BHK-Ms Biosynthesized ET-801: Recombinant ET-801 may be purified, among other techniques, using a one-step ion-exchange chromatography procedure as described recently (Spencer 2011). FVIII containing fractions may be identified by, for example but not limited to, one-stage coagulation assay and silver staining following sodium dodecyl sulfate polyacrylamide gel electrophoresis (SDS-PAGE). The specific activity of ET-801 may be calculated, for example, by using a molar extinction coefficient determined from the predicted tyrosine, tryptophan and cysteine content and absorbance at 280 nm (Pace C N, Vajdos F, Fee L, Grimsley G, Gray T. How to measure and predict the molar absorption coefficient of a protein. Protein Sci. 1995; 4(11):2411-23).

The specific activity of the final material may be defined, for example, as the weighted number average of the specific activities of the fVIII peak fractions, excluding any fractions demonstrating an absorbance at 280 nm less than 0.08 or an activation quotient less than 20. The purity of the ET-801 preparation may be assessed using multiple biochemical/physical techniques. As an example, SDS-PAGE and silver staining may be used to assess purity and processing. We expect, based on preliminary data, >95% of the purified protein material to be present in the heterodimeric (heavy chain/light chain) form characteristic of PACE/furin intracellular processing. We also may observe a small amount of unprocessed, single chain material, which is typically observed in our preparations of human, porcine and human/porcine hybrid fVIII (Spencer H T, Denning G, Gautney R E, Dropulic B, Roy A J, Baranyi L, et al. Lentiviral Vector Platform for Production of Bioengineered Recombinant Coagulation Factor VIII. Mol. Ther. 2011; Doering C, Parker E T, Healey J F, Craddock H N, Barrow R T, Lollar P. Expression and characterization of recombinant murine factor VIII. Thromb Haemost. 2002; 88(3):450-8; Doering C B, Parker E T, Healey J F, Craddock H N, Barrow R T, Lollar P. Expression and Characterization of Recombinant Murine Factor VIII. ThrombHaemost. 2002; 88(3):450-8; Doering C B, Healey J F, Parker E T, Barrow R T, Lollar P. Identification of porcine coagulation factor VIII domains responsible for high level expression via enhanced secretion. J Biol. Chem. 2004; 279 (8):6546-52, incorporated herein by reference).

ET-801 also may be incubated with thrombin prior to SDS-PAGE to confirm complete activation and the presence of only the A1, A2 and A3-C1-C2 bands, representative of heterotrimeric fVIIIa. The ET-801 preparation may be characterized by peptide mass fingerprinting (See, e.g., Mann M, Hendrickson R C, Pandey A. Analysis of proteins and proteomes by mass spectrometry. Annu Rev Biochem. 2001; 70:437-73, incorporated herein by reference). Briefly, the protein preparation may be digested and the masses of the peptide molecular ions may be determined thus yielding a peptide mass spectrum. More definitive identification may then be achieved by performing tandem mass spectrophotometric analysis of selected peptide ions. The data obtained may be used to verify the identity of ET-801, identify potential contaminants contained within the preparation and characterize post-translational modifications present.

The formation of high molecular-weight fVIII aggregates may complication of fVIII purification (Grillo A O, Edwards K L, Kashi R S, Shipley K M, Hu L, Besman M J, et al. Conformational origin of the aggregation of recombinant human factor VIII. Biochemistry. 2001; 40(2):586-95, incorporated herein by reference). Among other methods, a size-exclusion high performance liquid chromatography (HPLC) may be used to assay the ET-801 preparation for the presence of large fVIII aggregates.

Stability of Activated ET-801 following Thrombin Activation: Purified ET-801 may be screened for the rate of A2 subunit dissociation using a protocol described previously for the characterization of recombinant human, porcine ET-801, various human/porcine hybrid VIII constructs and murine fVIII (Doering C B, Parker E T, Healey J F, Craddock H N, Barrow R T, Lollar P. Expression and Characterization of Recombinant Murine Factor VIII. ThrombHaemost. 2002; 88(3):450-8; Doering C B, Healey J F, Parker E T, Barrow R T, Lollar P. Identification of porcine coagulation factor VIII domains responsible for high level expression via enhanced secretion. J Biol Chem. 2004; 279(8):6546-52; Doering C B, Healey J F, Parker E T, Barrow R T, Lollar P. High-level expression of recombinant porcine coagulation factor VIII. J Biol Chem. 2002; 277(41):38345-9; Parker E T, Doering C B, Lollar P. A1 subunit-mediated regulation of thrombin-activated factor VIII A2 subunit dissociation. J Biol. Chem. 2006, incorporated herein by reference).

For example, ET-801 may be diluted to 1, 20, 50 or 100 nM in 0.15 M NaCl, 0.02 HEPES, 2 mM $CaCl_2$ and activated with 100 nM thrombin for 30 sec. FVIIIa activity may be measured as a function of time by a chromogenic assay. Under these conditions, fVIII is completely activated by 30 sec and loss of activity in the assay is due entirely to decay of fVIIIa (Fay P J, Smudzin T M. Characterization of the interaction between the A2 subunit and A1/A3-C1-C2 dimer in human factor VIIIa. J Biol Chem. 1992; 267(19):13246-50; Lollar P, Parker C G. pH-dependent denaturation of thrombin-activated porcine factor VIII. J Biol Chem. 1990; 265(3):1688-92; Lollar P, Parker E T. Structural basis for the decreased procoagulant activity of human factor VIII compared to the porcine homolog. J Biol Chem. 1991; 266(19):12481-6; Lollar P, Parker E T, Fay P J. Coagulant properties of hybrid human/porcine factor VIII molecules. J Biol Chem. 1992; 267(33): 23652-7, incorporated herein by reference).

Determination of the efficacy of ET-801 in a murine model of hemophilia A: We have developed an efficacy model to assess the ability of fVIII to decrease the mortality or blood loss in E16 hemophilia A mice following tail transection (Parker E T, Lollar P. A quantitative measure of the efficacy of factor VIII in hemophilia A mice. Thromb Haemost. 2003; 89(3):480-5. Incorporated herein by reference). In this model, the mortality of hemophilia A mice is greater than 90% unless they receive fVIII prior to tail transection. This method may be used to determine the comparative efficacy of recombinant p-VIII to porcine plasma-derived fVIII by measuring the estimated dose that results in 50% survival ($ED_{50}$). This method may be used to determine the $ED_{50}$ for ET-801 in vivo. Briefly, E16 hemophilia A mice may first be administered an intraperitoneal injection of an anesthetic solution of 1.5 mg/kg droperidol/75 mg/kg ketamine. They may then be warmed under a 60 watt lamp for 3 minutes to dilate the tail veins. In a double-blinded design, varying amounts of ET-801, BDD p-fVIII, BDD h-fVIII or saline are administered intravenously into the tail vein. Fifteen minutes after the injection, mice may be placed in a 50 ml conical restraint tube, the distal 1 cm of tail is transected and the stump is placed into a 13×100 mm test tube containing 7.5 ml of 150 mM NaCl maintained in a 37° C. water bath. Surviving mice are weighed at 2, 4, 6 and 24 hours. Loss of body weight, as a quantitative surrogate measure of acute blood loss, will be used as a secondary efficacy variable. The $ED_{50}$ may be determined using the up-and-down method (Dixon W J. Staircase bioassay: the up-and-down method. Neurosci Biobehav Rev. 1991; 15(1):47-50, incorporated herein by reference). The standard deviation in all-or-none responses such as mortality data can be estimated using probit analysis.

CONCLUDING REMARKS

In summary, cells adapted to suspension according to the disclosed method, for example but not limited to BHK-Ms cells and HEK-293T cells represent a significant technological advance in biotherapeutic manufacturing and virus production.

ET-801 is a novel product in development for the treatment of hemophilia A that overcomes a major barrier to the treatment of affected patients, i.e. cost of fVIII products. Based on our preliminary data, we disclose and claim herein a method, system, and cell line that may be used to obtain significantly greater production levels for important biotherapeutics, such as but not limited to ET-801, than is achieved for currently marketed h-fVIII products. The combined technological advancements of high-expression fVIII elements, lentiviral-driven gene transfer and expression, and the utilization of the BHK-Ms cell platform for manufacturing will allow ET-801 to be marketed at a lower cost than current fVIII products and thus better support patients with hemophilia A, while subsequently providing an economic benefit through reduced subsidized healthcare costs.

We demonstrate above that the method disclosed herein may be generally used to modify different adherent cell lines to suspension culture. We illustrate that the resulting cell lines have the characteristics of increased yield of product over the parental and/or adherent cell line. We also disclose and characterize three specific cell lines made by the disclosed method, BHK-MS-310, BHK-MS-P14, and HEK-SC-293T. Each of these cells lines, being fully characterized above, is also available, among other locations, by contacting the inventors and/or assignee.

The disclosed method is novel over known methods for several reasons. Known methods of preparing suspension cells from adherent mammalian cell lines rely predominately on the use of microbeads, microcarriers, and other similar devices. Additionally, it has been reported that serum deprivation may transform some mammalian cell lines to suspension. The suspension cell lines resulting from the disclosed method exhibit a clumped state. (For a visual example of the clumped state, see FIG. 2 (slide marked "Day 10") and FIG. 4, for example, FIGS. 4(e) and 4(f). We herein characterize some advantages to clumped cell suspension over single cell suspensions that are currently known.

Furthermore, the method disclosed herein takes far less time and fewer materials than methods using microbeads and/or serum deprivation. We have demonstrated the novel characteristic of cells according to our disclosed method to be passable directly from serum containing into serum free media without the need for serial serum deprivation steps (e.g., serially transferring the cells to media containing reduced amounts of serum, e.g., 10% then 8% then 4% and etc. until they reach 0%). Removing the necessity for serum deprivation is a novel and surprising advantage which saves time and resources. Additionally, microbeads and microcarriers are extremely expensive, therefore our method which does not rely upon microbeads and/or microcarriers has, among other advantages, reduced cost over those methods which require microcarriers and/or microbeads.

REFERENCE TO DEPOSITED MATERIAL ACCORDING TO 13bis.3 (A)

On Jan. 25, 2012, a cell line assigned accession number ATCC PTA-12461 was deposited with American Type Culture Collection, 10801 University Boulevard, Manassas, Va. 20110, USA.

On Jun. 7, 2012, a cell line assigned accession number ATCC PTA-12593 was deposited with American Type Culture Collection, 10801 University Boulevard, Manassas, Va. 20110, USA.

While the foregoing written description of the invention enables one of ordinary skill to make and use what is considered presently to be the best mode thereof, those of ordinary skill will understand and appreciate the existence of variations, combinations, and equivalents of the specific exemplary embodiment and method herein. The invention should therefore not be limited by the above described embodiment and method, but by all embodiments and methods within the scope and spirit of the invention as claimed.

The invention claimed is:

1. Cell line ATCC PTA-12461.
2. The cell line of claim 1 characterized by about 5% to about 1000% greater polypeptide expression compared to the expression of the same polypeptide in an adherent cell line from which the suspension cell line is derived.
3. The cell line of claim 1 expressing the polypeptide fVIII.

* * * * *